(12) United States Patent
Flashaar et al.

(10) Patent No.: US 11,338,047 B2
(45) Date of Patent: May 24, 2022

(54) METHOD FOR DISINFECTING A WATER SYSTEM OF AN AIRCRAFT

(71) Applicant: Airbus Operations GmbH, Hamburg (DE)

(72) Inventors: Sebastian Flashaar, Hamburg (DE); Michael Rempe, Hamburg (DE); Axel Schreiner, Hamburg (DE)

(73) Assignee: Airbus Operations GmbH

( * ) Notice: Subject to any disclaimer, the term of this patent is extended or adjusted under 35 U.S.C. 154(b) by 297 days.

(21) Appl. No.: 16/419,200

(22) Filed: May 22, 2019

(65) Prior Publication Data

US 2019/0365936 A1 Dec. 5, 2019

(30) Foreign Application Priority Data

May 30, 2018 (DE) ..................... 10 2018 208 602.8

(51) Int. Cl.
*A61L 2/04* (2006.01)
(52) U.S. Cl.
CPC ..................... *A61L 2/04* (2013.01)
(58) Field of Classification Search
CPC ...... A61L 2/04; A61L 2/08; C02F 1/02; C02F 2303/04; C02F 2201/008; C02F 2209/02; B64F 5/30; B08B 9/032; B08B 9/08
See application file for complete search history.

(56) References Cited

U.S. PATENT DOCUMENTS

| 5,381,987 | A | * | 1/1995 | Carns ..................... B64F 1/22 244/50 |
| 8,083,861 | B2 | | 12/2011 | Labib et al. |
| 8,858,878 | B2 | | 10/2014 | Risch et al. |
| 10,131,554 | B2 | * | 11/2018 | Reiss ..................... C02F 1/4602 |
| 10,766,058 | B2 | * | 9/2020 | Boukari ................. B08B 13/00 |
| 11,000,041 | B2 | | 5/2021 | Benisti |

(Continued)

FOREIGN PATENT DOCUMENTS

DE 102009009938 A1 8/2010
DE 102010018273 A1 10/2011
(Continued)

OTHER PUBLICATIONS

Deutscher Verein des Gas-und Wasserfaches (DVGW), "Reinigung und Desinfektion von Trinkwasser-Installationen," Worksheet W 557, Oct. 2012 [publication from the German Association for the Gas and Water Sector (DVGW) entitled "Cleaning and Disinfection of Drinking Water Installations", Worksheet W 557, Oct. 2012].

(Continued)

*Primary Examiner* — Regina M Yoo
(74) *Attorney, Agent, or Firm* — Lerner, David, Littenberg, Krumholz & Mentlik, LLP

(57) ABSTRACT

A method for disinfecting a water system of an aircraft includes letting-in of hot water at an inlet of the water system by a first ground service unit; flushing the hot water from the inlet, through water pipes of the water system, to an outlet of the water system; and letting-out of the hot water at the outlet, by the first ground service unit or a second ground service unit; the hot water being flushed into the inlet and out of the outlet over a predefined disinfection period; and the hot water being provided at the inlet via a continuous-flow heater of the first ground service unit.

10 Claims, 5 Drawing Sheets

(56) References Cited

U.S. PATENT DOCUMENTS

| | | |
|---|---|---|
| 2004/0217183 A1 | 11/2004 | Bae et al. |
| 2005/0103726 A1* | 5/2005 | Palm .......................... C02F 1/78 |
| | | 210/760 |
| 2005/0126927 A1 | 6/2005 | Lindauer et al. |
| 2013/0094994 A1 | 4/2013 | Risch et al. |
| 2014/0230845 A1 | 8/2014 | Boukari |
| 2016/0236247 A1 | 8/2016 | Boukari |
| 2016/0251090 A1 | 9/2016 | Boukari |
| 2018/0085796 A1 | 3/2018 | Boukari |
| 2018/0334402 A1 | 11/2018 | Williams et al. |
| 2018/0360047 A1 | 12/2018 | Benisti |

FOREIGN PATENT DOCUMENTS

| | | |
|---|---|---|
| EP | 1025917 A1 | 8/2000 |
| FR | 2975928 A1 | 12/2012 |
| FR | 3008632 A1 | 1/2015 |
| WO | 2006100094 A1 | 9/2006 |
| WO | 2010142924 A2 | 12/2010 |
| WO | 2018234218 A1 | 12/2018 |

OTHER PUBLICATIONS

Co-Pending U.S. Appl. No. 16/417,887, filed May 21, 2019.
Search Report for GB1907607.4 dated Nov. 14, 2019.
Search Report for GB1907608.2 dated Nov. 20, 2019.
Extended Search Report including Written Opinion for French Application No. 1905510 dated Aug. 31, 2021; 9 pages.

* cited by examiner

METHOD FOR DISINFECTING A WATER SYSTEM OF AN AIRCRAFT

FIELD OF THE INVENTION

The present invention relates to a method for disinfecting a water system of an aircraft.

BACKGROUND OF THE INVENTION (Drinking-)water systems of modern passenger aircraft typically comprise an extensive network of water pipes that extends from inlet and outlet openings on the outside of the aircraft fuselage, via distributer pipes through the aircraft fuselage, to consumers such as on-board galleys, sanitary facilities, etc. within a passenger cabin. In addition, such passenger aircraft normally have at least one water tank, for supplying the water system, which for example may have a capacity of approximately 1000 litres.

The publication Deutscher Verein des Gas-und Wasser-faches (DVGW), "Reinigung und Desinfektion von Trinkwasser-Installationen," Worksheet W 557, October 2012, describes the practical execution of cleaning and disinfection measures, as well as preventative measures for preventing contamination of drinking-water installations. Described as one possibility for disinfection is thermal disinfection, in which hot water is flushed through an entire drinking-water installation. Another mentioned possibility for disinfection, which is used in very many instances in the aviation sector, is that of chemical disinfection, in which disinfecting chemicals such as, for example, sodium hypochlorite, chlorine dioxide and hydrogen peroxide are used, in particular application concentrations, for conditioning the drinking-water installation. It is also occasionally proposed, especially in medical and industrial applications, to use hot steam at the boiling temperature of water (e.g. 100° C. at 1 atm) for disinfection.

Usually, for the thermal and chemical disinfection of the water tanks of passenger aircraft, ground service units (ground service equipment, GSE) such as, for example, tank wagons having sufficiently large tanks, are used in order to provide a corresponding quantity of a hot water supply, or of a disinfection mixture, such that the water tank of an aircraft, together with the feed pipes and discharge pipes, as well as the pipe network of the aircraft, can be completely filled with the liquid. This requires large quantities of liquid to be provided, and heated if appropriate. Moreover, several operations of flushing the water tanks and/or the water pipes may be necessary, as a result of which the disinfection, together with an occasionally performed bleeding operation, etc., can occupy an entire day.

BACKGROUND OF THE INVENTION

Against this background, aspects of the present invention may provide simpler, more rapid and more cost-effective solutions for disinfecting water systems of aircraft.

Provided accordingly is a method for disinfecting a water system, in particular a drinking-water system, of an aircraft. The method comprises letting-in of hot water at an inlet of the water system by a first ground service unit; flushing the hot water from the inlet, through water pipes of the water system, to an outlet of the water system; and letting-out of the hot water at the outlet, by the first ground service unit or a second ground service unit; the hot water being flushed into the inlet and out of the outlet over a predefined disinfection period; and the hot water being provided at the inlet via a continuous-flow heater of the first ground service unit.

An idea on which the present invention is based is to avoid the use both of chemicals and of storage tanks, in that hot water is produced directly in situ by a ground service unit (GSE) by means of a continuous-flow heater, and is introduced into the pipes to be disinfected. For this purpose, a GSE requires only a connection to a water supply, without the need for a large liquid tank, not to mention heating it, with a large consumption of energy. In this way, the GSE can be of a compact and flexible design, with the result that the disinfection process can be used selectively in selected critical (pipe) regions in a manner that saves time, costs and energy. Furthermore, a (mobile) deployment in an aviation-specific work environment can be facilitated, or rendered economically feasible, as a result of a compact design of the GSE, with only a small (electric) power consumption. For example, it is possible to use a standard commercial, electrically operated continuous-flow heater, which may be characterized by a compact size and a low power consumption. For example, continuous-flow heaters having electric power ratings of, for instance, 20 kW or less may be used.

Advantageous designs and developments become evident from the further dependent claims and from the description with reference to the figures.

According to a development, the hot water may have a water temperature of between 60° C. and 80° C. On the one hand, a disinfection process is faster, the higher the temperature of the water. On the other hand, the aircraft components of modern, lightweight aircraft frequently only have a limited temperature resistance capacity, precluding water temperatures of 80° C. or more, i.e. in particular boiling water. Accordingly, in this development, an advantageous compromise is found between a disinfection period that is as short as possible and a least possible impairment of the affected aircraft structures, such as pipes and surrounding regions. In this case it can be ensured, in particular, that the hot water has a temperature of at least 60° C. in the entire flushed-through region of the water pipes. For example, the hot water can be provided at a temperature of approximately 70° C., and flushed through the water pipes.

In the present case, it is necessary to distinguish a disinfection from a sterilization. A disinfection, within the context of the description, denotes an action upon a water supply system, or upon a medium such as drinking water, in such a manner that they are put into a state in which they can no longer cause infection. A disinfection of drinking-water installations in this sense can be performed at temperatures considerably lower than the boiling point of water, in particular at temperatures down to approximately 60° C. Accordingly, a sterilization denotes not only an adequate reduction or eradication of germs and pathogens, but also a practically complete removal or eradication of all microorganisms in each development stage, including their quiescent stages (e.g. spores). A sterilization is therefore typically performed at very high temperatures, e.g. 121° C., not least in order to keep the required process duration as short as possible (e.g. 3 minutes at 121° C.).

According to a development, the letting-out of the hot water at the outlet may be controlled by means of a pressure-maintaining means of the first ground service unit and/or of the second ground service unit. A pressure-maintaining means, for example a pressure-maintaining valve, may be used, inter alia, to let out the hot water at a controlled pressure and, in such a manner, to ensure a flow of liquid that is as uniform and well-defined as possible through the pipes to be disinfected and the draw-off points connected in the aircraft.

According to a development, the water pipes may comprise inlet pipes, distribution pipes, supply pipes, outlet pipes and/or consumer pipes. Furthermore, the water pipes may comprise draw-off points or the like. For example, it is not only the inlet and outlet pipes adjoining an inlet or an outlet, respectively, and the supply or distribution pipes adjoining them and running, for example, beneath a cabin floor, that can be flushed through. Consumer pipes of consumers within a passenger cabin, cockpit and/or cargo hold, e.g. on-board galleys, sanitary installations, etc., that are connected to the supply pipes, can likewise additionally be disinfected.

According to a further development, pressure may be applied to a tank section of the water system during the flushing of the hot water, in order to keep the hot water away from the tank section. This development offers the advantage that only selected regions of the water system can be disinfected, independently of the tank section and thus, in particular, independently of the at least one tank connected there. In particular, in this development it is thus not necessary for the tank or tanks of the aircraft, which typically hold over 1000 litres, to be filled with hot water. The method can thus be performed in a particularly time-efficient and cost-effective manner. Owing to the utilization of the flow-through, or flush-through, principle, the sought temperature range of the hot water can be attained very rapidly within the water pipes, such that the disinfection time period can be kept extremely short, e.g. less than one hour, for example 30 minutes.

According to a development, compressed air, for the application of compressed air to the tank section, may be provided via a compressed-air supply of the first ground service unit and/or the second ground service unit. For example, the respective ground service unit may comprise a pressure-maintaining means, via which a certain static air pressure can be ensured within the tank section, i.e. in particular within the tank or tanks, in order to deflect the water flow into the pipe system away from the tanks.

According to a development, the compressed air may be let into the tank section via a tank outlet of the tank section. For example, an overflow discharge, or overflow outlet, of a tank section may be used for this purpose.

According to a development, a hot-water circuit may be formed from the inlet, through a tank section to the outlet, and back to the inlet. This development is especially suitable for a disinfection of a tank section, and of the at least one tank connected therein, that is as efficient, rapid and cost-effective as possible. In this case, the at least one tank can be completely flushed through, or flooded, with hot water. For this purpose, a GSE having a compact continuous-flow heater and corresponding means for water circulation can continuously flush water through the tank section, in order to bring the water in the entire tank section to a desired temperature of between 60° C. and 80° C., e.g. 70° C. The hot water can be circulated in the hot-water circuit for the predefined disinfection period. In this development, there is thus no need for large external tanks, e.g. of 1000 litres or more, for providing the necessary filling quantity of hot water. The development can thus be implemented in a particularly efficient and practical manner by means of mobile GSEs. In such a manner, even very large tanks, of 1500 litres or more, can be disinfected in a few hours, solely on the basis of a continuous-flow heater having a low power rating, e.g. having a power consumption of 20 kW, whereby especially application in an aviation-specific work environment is facilitated, or rendered economically feasible.

According to a development, the hot-water circuit may be closed between the outlet and the inlet by means of a circulation pump of the first ground service unit. A circulation pump, which can easily be realized, for example, in a small, compact and mobile ground service unit, represents a possible technical means for realizing the hot-water circuit explained above.

According to a development, a tank outlet of the tank section may be used as an outlet. Moreover, for example an inlet of the aircraft, which, like the tank outlet, is present as standard in any case, may be used as an inlet. Thus, no special provisions need be made on the aircraft in order to realize the hot-water circuit.

The above designs and developments can be combined with each other in any manner, insofar as appropriate. Further possible designs, developments and implementations of the invention also comprise combinations, not stated explicitly, of features of the invention described previously or in the following with respect to the exemplary embodiments. In particular, persons skilled in the art will also add individual aspects, as improvements or supplements, to the respective basic form of the present invention.

BRIEF DESCRIPTION OF THE DRAWINGS

The present invention is explained in greater detail in the following on the basis of the exemplary embodiments specified in the schematic figures. There are shown.

DETAILED DESCRIPTION

Figure 1:
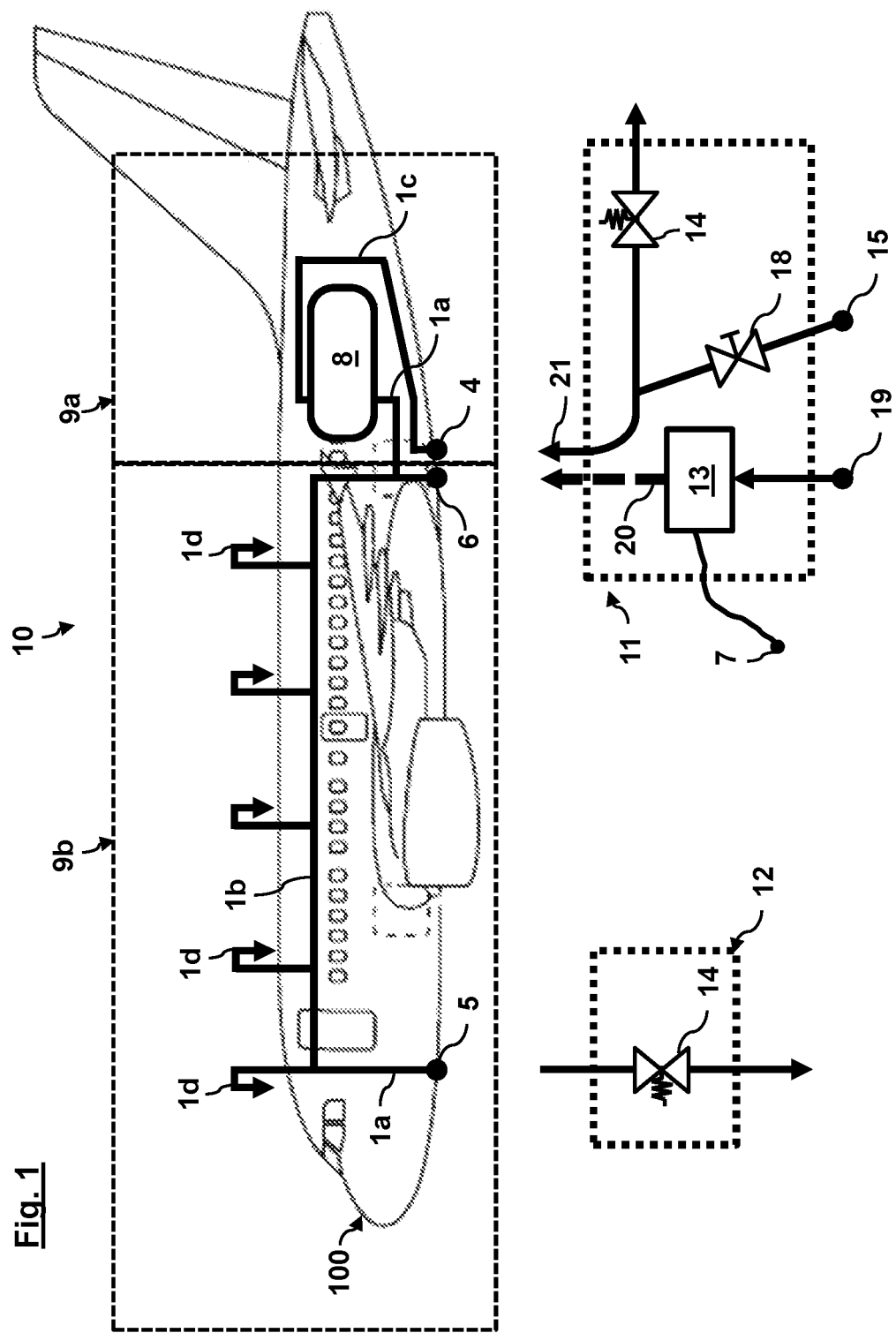
FIG. 1 schematic side view of an aircraft having a water system, before the execution of a method for disinfecting according to an embodiment of the invention.

The accompanying figures are intended to impart a further understanding of the embodiments of the invention. They illustrate embodiments and serve, in combination with the description, to explain principles and concepts of the invention. Other embodiments, and many of the stated advantages, become evident with regard to the drawings. The elements of the drawings are not necessarily shown true to scale in relation to each other.

In the figures of the drawing, elements, features and components that are the same, have the same function and act in the same manner—unless stated otherwise—are in each case denoted by the same references.

Figure 2:
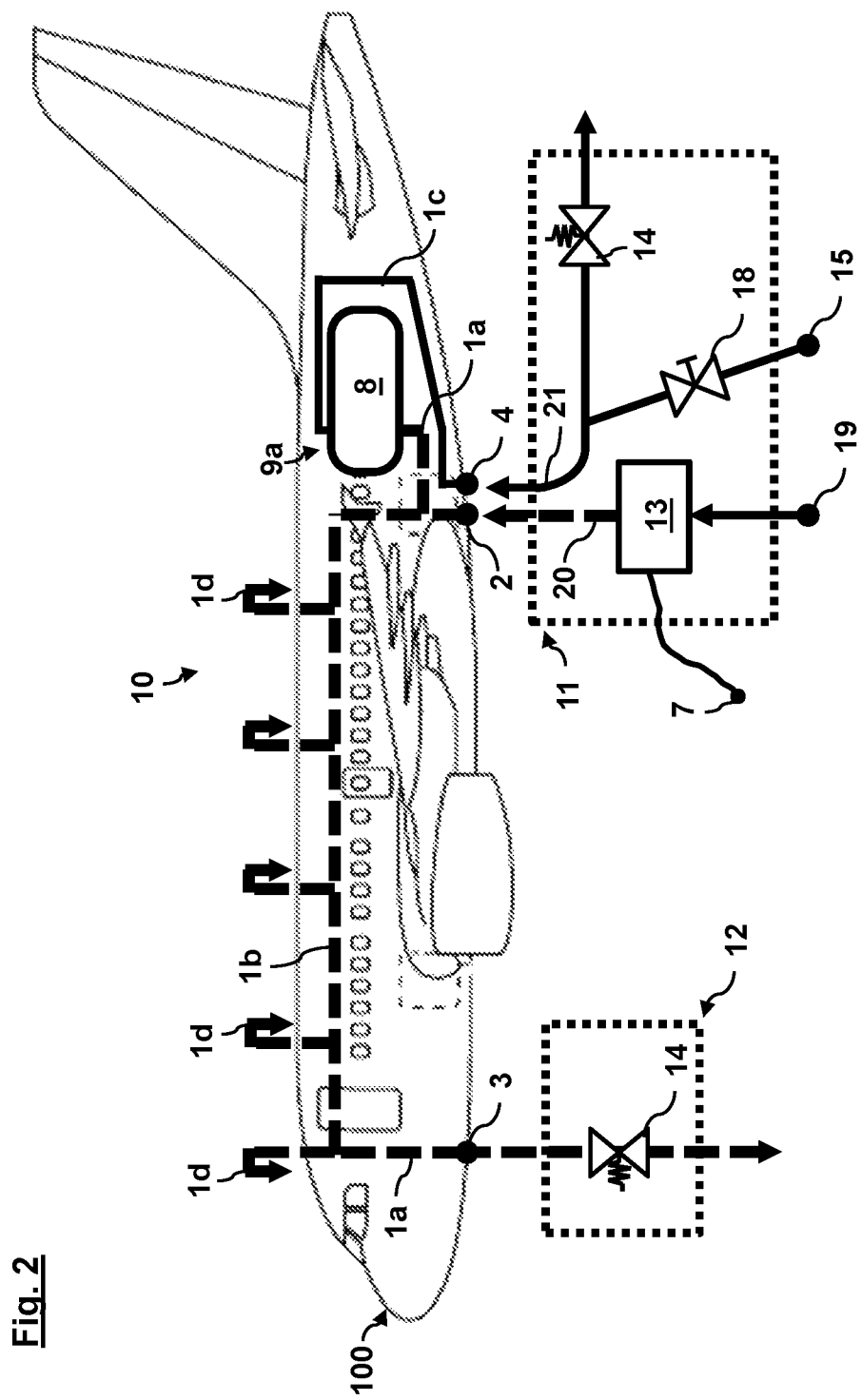
FIG. 2 schematic side view of the aircraft from FIG. 1, during the execution of the method.
Figure 5:
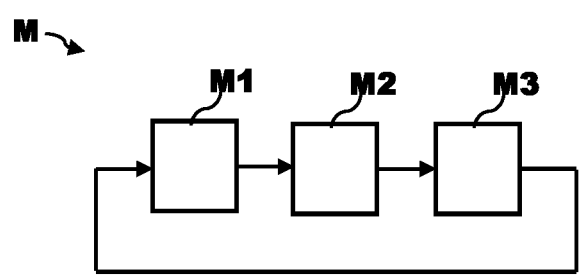
FIG. 5 schematic flow diagram of a method for disinfecting a water system of an aircraft according to an embodiment of the invention.

FIGS. 1 and 2 show schematic side views of an aircraft 100 having a water system 10, during the execution of a method M for disinfecting according to an embodiment of the invention. FIG. 5 shows a schematic flow diagram of the method M.

The aircraft 100, e.g. a passenger aircraft, comprises a water system 10, in particular a drinking-water system, having a network of water pipes 1*a-d* and a tank 8, which is located in a tank section 9a of the water system 10. Purely by way of example, the aircraft 100 comprises a front, front-side water connection 5 and a rear, rear-side water connection 6, which in principle can each be used as an inlet and/or outlet. From the water connections 5, 6, differing water pipes 1a-d, including inlet pipes 1a, distributer pipes or supply pipes 1b, outlet pipes 1c and consumer pipes 1d lead, in the manner of a network, through a fuselage of the aircraft 100, both in the tank section 9a and in an adjoining distribution section 9b. The consumer pipes 1d in this case may lead, for example, to consumers in a passenger cabin, a cockpit or a cargo hold, etc. e.g. to an on-board galley, to a sanitary installation, such as a shower, a washroom, a toilet or the like. The distributer pipes or supply pipes 1b may run, for example, beneath a cabin floor, along the latter (not shown), and in turn be connected to the inlet pipes 1a and outlet pipes 1c that, in turn, lead to the water connections 5, 6. Furthermore, the tank section 9a of the water system 10 is likewise connected to the water pipes 1a-d of the distribution section 9b of the water system 10. In addition, the tank section 9a has a separate tank discharge 4, which is realized as an overflow, or bleed, connection of the tank 8. The tank 8 may have, for example, a capacity of 1000 litres or more. In principle, it must be pointed out that the water connections 5, 6, or tank discharges 4, the water pipes 1a-d, and the tank 8, that are specifically represented in this exemplary embodiment are to be understood merely as being purely exemplary. On the basis of the present teaching, persons skilled in the art will conclude that the specific configuration of these components can be designed differently in alternative embodiments. For example, more than two water connections 5, 6 may be provided, the courses of the water pipes 1a-d, or their connection points, may be different, or more than one tank 8 may be installed, etc. Moreover, the tank 8, or the tank section 9a, may be located at a different position within the aircraft 100.

FIG. 1 additionally shows a first ground service unit 11, e.g. a ground vehicle, and a second ground service unit 12, e.g. a further ground vehicle. The first ground service unit 11 comprises a continuous-flow heater 13 that is supplied with electrical energy via an electricity supply 7. The continuous-flow heater 13 is connected to a water supply 19 and heats the water, delivered from the water supply 19, to a temperature of between 60° C. and 80° C., e.g. 70° C. The hot water 20 can be used by the first ground service unit 11 to fill the water system 10 of the aircraft 100 (see FIG. 2). The first ground service unit 11 is additionally designed to provide compressed air 21 from a compressed-air supply 15. The compressed air 21 may optionally be connected-in or disconnected by means of a stop valve 18. The first ground service unit 11 additionally has a pressure-maintaining means 14, by means of which an air pressure can be regulated, or can be set at a fixed value. The second ground service unit 12 likewise comprises a pressure-maintaining means 14, via which hot water can be let out of the aircraft 100 in a controlled manner, as is explained in the following with reference to FIG. 2.

In FIG. 2, the first ground service unit 11 is connected to the rear water connection 6 for the purpose of introducing the hot water 20, and to the tank outlet 4 for the purpose of introducing the compressed air 21. The rear water connection 6 in this case is thus used as an inlet 2 for the hot water 20. In addition, in FIG. 2 the second ground service unit 12 is connected to the front water connection 5 for the purpose of letting out hot water 20, which is routed from the inlet 2, via the water pipes 1a-d, to the front water connection 5. In this example, the front water connection 5 thus serves as an outlet 3.

In the example of FIGS. 1 and 2, the water system 10 of the aircraft 100 is disinfected in that, under M1, the hot water 20 is let in at the inlet 2 by the first ground service unit 11, then flushed from the inlet 2, through the water pipes 1a, 1b, 1d of the distribution section 9b, to the outlet 3, and at the outlet 3 is let out again by the second ground service unit 12 (in this case, clearly, some of the hot water 20 can be flushed out, for example, at the consumer pipes 1d). The flow of the hot water 20 is indicated in FIG. 2 by thick broken lines. This flushing operation is performed over a predefined disinfection period. At the same time, compressed air is applied by the first ground service unit 11, via the tank outlet 4 and the outlet pipe 1c, to the tank section 9a, including the tank 8, in order to keep the hot water 20 away from the tank section 9a (see FIG. 2, where the thick broken line does not lead into the tank section 9a).

As a result, a pragmatic disinfection method is provided for disinfecting the water pipes 1a, 1b, 1d of the distribution section 9b of the water system 10, which is rapid, cost-effective and energy-efficient. This is achieved, inter alia, in that filling of the tank 8 with hot water 20 is avoided. Owing to the flow-through principle used, a sufficient high temperature, of at least 60° C., can be attained very rapidly in the water pipes 1a, 1b, 1d, e.g. within 10 to 30 minutes, depending on the size of the aircraft 100. Accordingly, the disinfection period can be kept very much shorter than in conventional disinfection methods, e.g. significantly less than one hour. In many applications, this selective disinfection of the water pipes 1a, 1b, 1d, outside of a tank section 9a, may already be sufficient to achieve a hygienically acceptable state of the complete water system 10, e.g. if the tank 8 is new and/or in a sufficiently clean state. In principle, the explained method may likewise be used for localised regions of an aircraft 100, e.g. an individual on-board galley and/or an individual sanitary installation, provided that the corresponding connections and water pipes are present to enable a dedicated flush-through.

Figure 3:
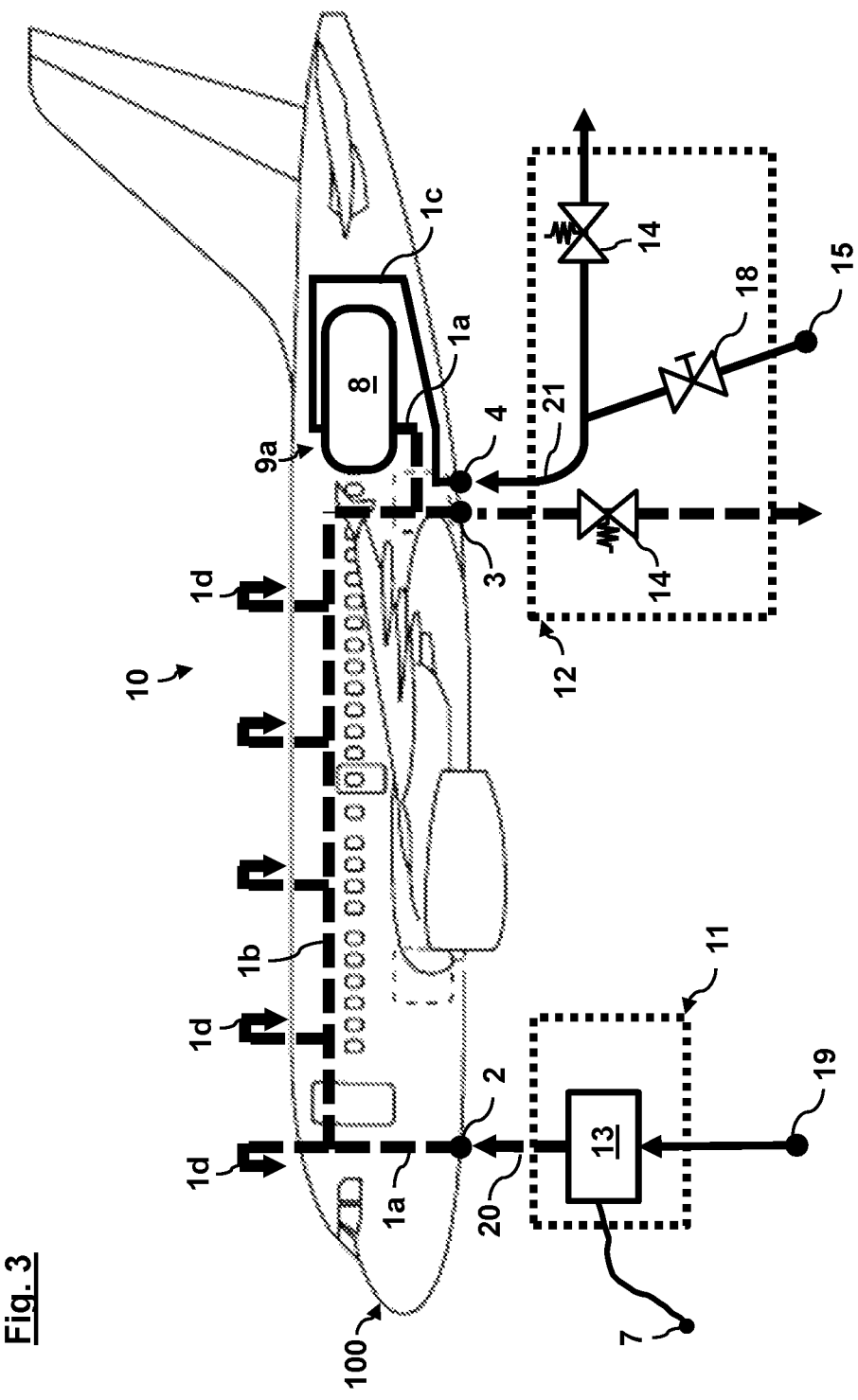
FIG. 3 schematic side view of an aircraft having a water system, during the execution of a method for disinfecting according to a further embodiment of the invention.

An alternative exemplary variant of the method M is represented in FIG. 3, the aircraft 100 and its water system 10 being realized in a manner identical to that in FIGS. 1 and 2. Unlike the embodiment in FIGS. 1 and 2, the first ground service unit 11 is connected to the front water connection 5, which accordingly now serves as an inlet 2. On the other hand, the second ground service unit 12 is connected to the rear water connection 6, i.e. the latter serves as an outlet 3. In this example, owing to the changed basic arrangement, the second ground service unit 12 is now connected to a compressed-air supply 15, on the one hand, and to the tank outlet 4, on the other hand. In this example, it would optionally be possible to dispense with the compressed-air supply of the tank 8 and, for example, for only the tank outlet 4 to be closed with a cap or the like. Apart from these differences, the method M proceeds as that in FIGS. 1 and 2.

Figure 4:
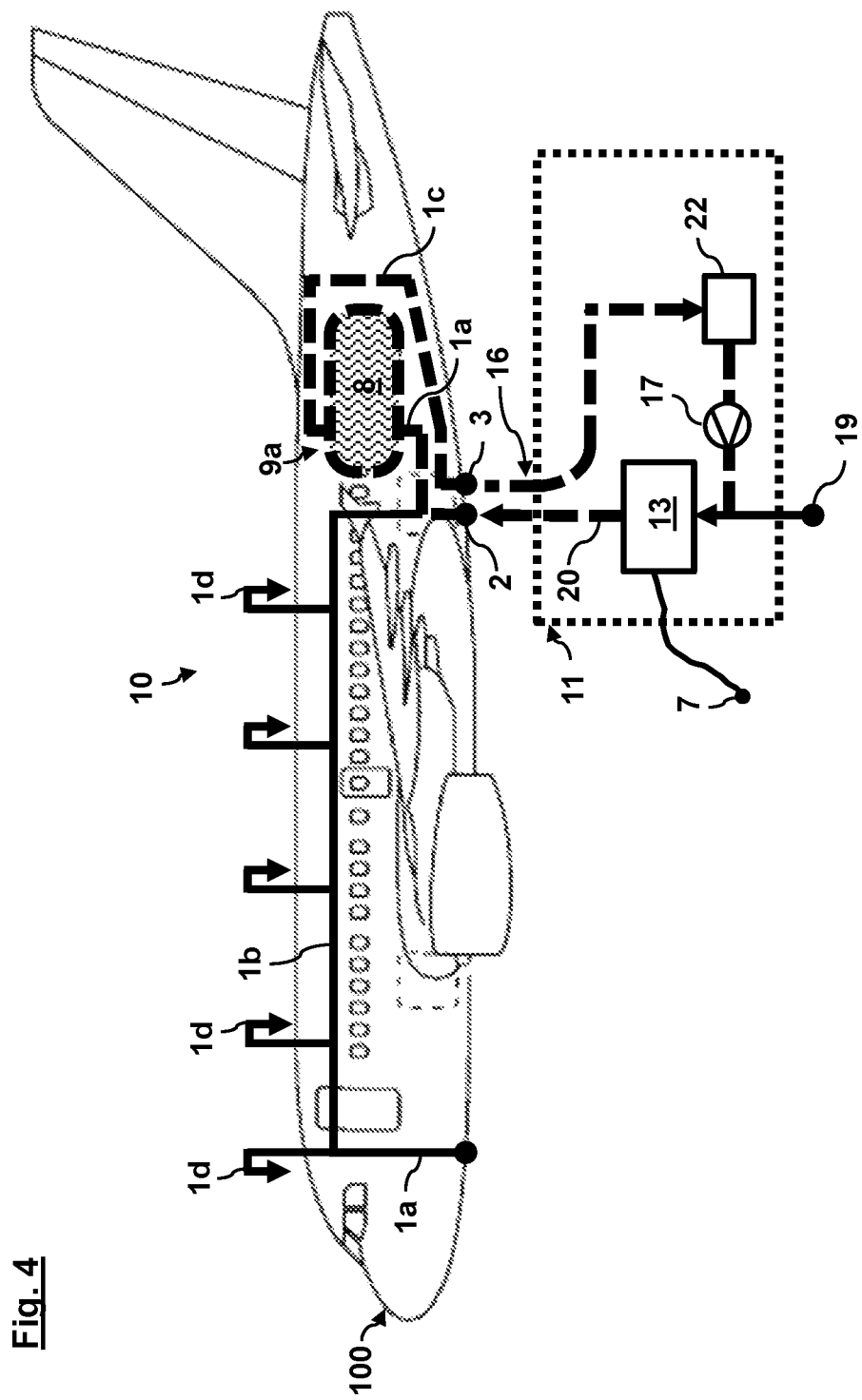
FIG. 4 schematic side view of an aircraft having a water system, during the execution of a method for disinfecting according to a further embodiment of the invention.

A further alternative exemplary variant of a disinfection method M is represented in FIG. 4, the aircraft 100 and its water system 10 being realized in a manner identical to that in FIGS. 1 and 2. In this exemplary embodiment, only a first ground service unit 11 is used. The first ground service unit 11 is connected to the rear water connection 6 and the tank outlet 4, the rear water connection serving as an inlet 2, and the tank outlet 4 as an outlet 3. The first ground service unit 11 comprises, besides a continuous-flow heater 13, a circulation pump 17, which is connected to the outlet 3 via an interposed bleed valve 22. The first ground service unit 11 heats water from a water supply 19, and feeds it, at the inlet 2, into the water pipe 1a and the tank 8 of the tank section 9a of the water system 10, from which it emerges again at the outlet 3, via the water pipe 1c. By means of the circulation pump 17, the hot water 20, in turn, is returned to the continuous-flow heater 13, with the result that a hot-water circuit 16 is created by the tank section 9a and the first ground service unit 11. Here, the flow of the hot water 20 is represented, in a manner similar to that in FIGS. 2 and 3, by a thick broken line.

In this example, a disinfection method is provided for disinfecting specifically a tank section 9a, together with its water pipes 1a, 1c and tanks 8, that is rapid, cost-effective and energy-efficient. In this case, unlike the examples from FIGS. 1 to 3, the tank 8 is completely flooded with hot water 20, with the result that the method M does not proceed as rapidly as the previous methods. However, the method M is nevertheless significantly more cost-effective and energy-efficient than conventional thermal methods for disinfecting a tank 8. This is achieved, inter alia, in that a water circuit is created by the tank 8 and the tank section 9a, in which the water can be heated gradually, via the continuous-flow heater 13, to a water temperature of between 60° C. and 80° C., e.g. 70° C., in an energy-efficient manner. Thus, just as in the previous methods M, large heated external tanks are avoided, which, in the case of conventional methods, must have a capacity corresponding to that of the tank 8 of the aircraft 100. Moreover, the first ground service unit 11 can be of a compact and mobile design, since no external liquid tanks or high-power heating devices are required. The larger the tank 8 of the aircraft 100, the more these advantages come to the fore.

In the preceding detailed description, various features have been combined in one or more examples in order to achieve a more concise presentation. It should be understood, however, that the above description is of a merely illustrative nature, and is by no means restrictive. It serves to cover all alternatives, modifications and equivalents of the various features and exemplary embodiments. By consideration of the above description, many other examples will immediately and directly become obvious to persons skilled in the art on the basis of their specialist knowledge.

For example, the number of connections used, the direction of flow of the hot water, and the course of the water pipes may be adapted to the existing configuration of the aircrafts to be disinfected.

The exemplary embodiments have been selected and described in order to present in the best possible manner the principles on which the invention is based, and their practical application possibilities. Consequently, persons skilled in the art can optimally modify and use the invention and its various exemplary embodiments with regard to the intended application. In the claims and in the description, the terms "containing" and "having" are used as neutral expressions for the corresponding terms "comprising". Furthermore, use of the terms "a" and "an" is not intended fundamentally to preclude a plurality of features and components described in such a manner.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

LIST OF REFERENCES 1a-d water pipe
1a inlet pipe
1b distributer pipe
1c outlet pipe
1d consumer pipe
2 inlet
3 outlet
4 tank outlet
5 front water connection
6 rear water connection
7 electricity supply
8 tank
9a tank section/rear section
9b distribution section
10 water system
11 first ground service unit
12 second ground service unit
13 continuous-flow heater
14 pressure-maintaining means
15 compressed-air supply
16 hot-water circuit
17 circulation pump
18 stop valve
19 water supply
20 hot water
21 compressed air
22 bleed valve
100 aircraft
M method
M1 method step
M2 method step
M3 method step

The invention claimed is:

1. A method for disinfecting a water system of an aircraft, comprising:
    letting-in hot water at an inlet of the water system by a first ground service unit;
    flushing the hot water from the inlet, through water pipes of the water system, to an outlet of the water system; and
    letting-out the hot water at the outlet, by the first ground service unit or a second ground service unit;
    wherein the hot water is flushed into the inlet and out of the outlet over a predefined disinfection period; and
    the hot water is provided at the inlet via a continuous-flow heater of the first ground service unit.

2. The method according to claim 1, wherein the hot water has a water temperature of between 60° C. and 80° C.

3. The method according to claim 1, wherein the letting-out the hot water at the outlet is controlled by a pressure-maintaining means of the first ground service unit and/or of the second ground service unit.

4. The method according to claim 1, wherein the water pipes comprises at least one of inlet pipes, distribution pipes, outlet pipes and consumer pipes.

5. The method according to claim 1, wherein pressure is applied to a tank section of the water system during the flushing of the hot water, in order to keep the hot water away from the tank section.

6. The method according to claim 5, wherein compressed air, for application of compressed air to the tank section, is provided via a compressed-air supply of the first ground service unit and/or the second ground service unit.

7. The method according to claim 6, wherein the compressed air is let into the tank section via a tank outlet of the tank section.

8. The method according to claim 1, wherein a hot-water circuit is formed from the inlet, through a tank section to the outlet, and back to the inlet.

9. The method according to claim 8, wherein the hot-water circuit is closed between the outlet and the inlet by a circulation pump of the first ground service unit.

10. The method according to claim 8, wherein a tank outlet of the tank section is used as the outlet.

* * * * *